United States Patent [19]

Gottschlich et al.

[11] 4,031,230
[45] June 21, 1977

[54] NOVEL PENICILLINS AND THEIR PREPARATION

[75] Inventors: Rudolf Gottschlich; Werner Rogalski; Rolf Bergmann; Rosmarie Steinigeweg; Helmut Wahlig, all of Darmstadt, Germany

[73] Assignee: Merck Patent Gesellschaft mit beschrankter Haftung, Darmstadt, Germany

[22] Filed: Oct. 22, 1975

[21] Appl. No.: 624,763

[30] Foreign Application Priority Data

Aug. 9, 1975    Germany ........................ 2535655
Oct. 25, 1974   Germany ........................ 2450668

[52] U.S. Cl. ........................ 424/271; 260/239.1; 260/295 F; 260/295 T; 260/295 A; 260/295 CA; 260/294.8 R; 260/294.8 B; 260/294.8 C
[51] Int. Cl.² .............. C07D 499/68; A61K 31/43
[58] Field of Search ............. 260/239.1; 424/271

[56] References Cited

UNITED STATES PATENTS

| | | |
|---|---|---|
| 3,720,664 | 3/1973 | Erickson .................. 260/239.1 |
| 3,870,709 | 3/1975 | Hamanaka ................ 260/239.1 |
| 3,935,189 | 1/1976 | Fenes et al. .............. 260/239.1 |
| 3,939,150 | 2/1976 | Murakami et al. ......... 260/239.1 |
| 3,945,995 | 3/1976 | Yamada et al. ............ 260/239.1 |
| 3,951,955 | 4/1976 | Tobiki et al. .............. 260/239.1 |
| 3,954,733 | 5/1976 | Tobiki et al. .............. 260/239.1 |

Primary Examiner—Gerald A. Schwartz
Attorney, Agent, or Firm—Millen & White

[57] ABSTRACT

Penicillins of the formula

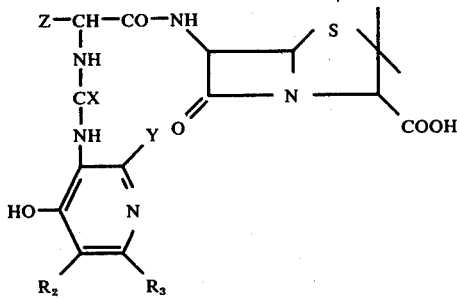

wherein X is O or S; Y is H or alkyl; Z is

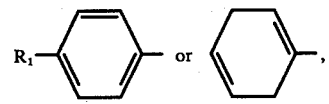

$R_1$ is H or OH; and $R_2$ and $R_3$ each are H or wherein X is O or S; Y is H or alkyl; $R_2$ and $R_3$ each are H or taken together with the carbons to which they are attached form an aromatic six-membered carbocyclic or N-heterocyclic ring and alkyl, alkoxy, dialkylamino or halogen derivatives thereof are active against Gram-positive and Gram-negative bacteria.

100 Claims, No Drawings

NOVEL PENICILLINS AND THEIR PREPARATION

BACKGROUND OF THE INVENTION

This invention relates to novel penicillins, to pharmaceutical compositions comprising them, and to processes for their preparation and use.

SUMMARY OF THE INVENTION

In a composition aspect, this invention relates to novel penicillins of Formula I

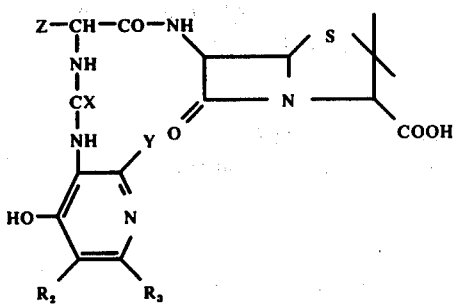

wherein X is O or S, Y is H or alkyl; Z is

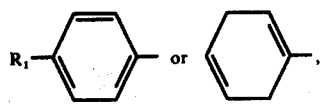

$R_1$ is H or OH, and $R_2$ and $R_3$ each are H or collectively with the carbons to which they are attached form a first benzene or pyridine ring which is unsubstituted, substituted by up to two of alkyl, alkoxy of 1–4 carbon atoms, dialkylamino or halogen, wherein alkyl and alkoxy in each instance are of 1 to 4 carbon atoms or is fused at two adjacent carbons to a second benzene or pyridine ring; or an in vivo hydrolyzable and physiologically acceptable ester thereof; or a physiologically acceptable salt of either.

In another composition aspect, this invention relates to pharmaceutical compositions comprising a novel penicillin of this invention.

In a further composition aspect, this invention relates to novel intermediates for the production of the novel penicillins of this invention.

In process aspects, this invention relates to processes for the production and use of the novel penicillins of this invention.

DETAILED DISCUSSION

In the compounds of Formula I, $R_2$ and $R_3$ each are H or together are a —CH=CH—CH=CH— group or corresponding group in which one CH thereof is replaced by N and/or 1 H atom thereof is replaced by $R_4$ or 2 H atoms thereof are replaced by $R_4$ and $R_5$, wherein $R_4$ and $R_5$ each are alkyl, alkoxy, dialkylamino, halogen or $R_4$ and $R_5$ collectively are a second —CH=CH—CH=CH— group or a corresponding group in which one CH group thereof is replaced by N, and wherein alkyl and alkoxy in each instance are of 1 to 4 carbon atoms.

The novel penicillins of Formula I and their esters which can be readily hydrolyzed in vivo and the physiologically acceptable salts of each are well tolerated and possess valuable pharmacological properties. They possess good activity, both in vitro and in vivo, against pathogenic micro-organisms, for example, Gram-positive or Gram-negative bacteria, and are particularly distinguished by a broad spectrum of action. These compounds are, in particular, extremely active against micro-organisms of the genera Pseudomonas, for example, Pseudomonas aeruginosa, and Proteus, for example, Proteus vulgaris and Proteus mirabilis. They also are very active against, for example, Escherichia coli and Klebsiella pneumoniae. These activities can be demonstrated, for example, in the customary way on bacterial cultures in vitro. Activity against bacteria which are resistant to other penicillins is also found.

The chemotherapeutic activity in vivo is preferably determined in mice. Pharmacokinetic experiments, for example, determinations of the concentrations of the active compounds in serum, from which the biological half life can be calculated, are preferably carried out in dogs. Tests in rats or other mammals can be employed, but, in general, are not required.

The novel penicillins can be used as medicaments in human and veterinary medicine, particularly for combating bacterial infections. They can also be used as intermediates for the preparation of other medicaments.

The alkyl and alkoxy groups of the compounds of Formula I are of 1–4 carbon atoms, but preferably are of 1 to 2 carbon atoms. Accordingly, alkyl is preferably methyl or ethyl, but can also be n-propyl, isopropyl, n-butyl, isobutyl, sec.-butyl or tert.-butyl. Alkoxy is preferably methoxy or ethoxy, but can also be n-propoxy, isopropoxy, n-butoxy, isobutoxy, sec.-butoxy or tert.-butoxy.

Dialkylamino can be of up to 8 carbon atoms, but those of up to 4 carbon atoms are preferred. Thus, dialkylamino is preferably dimethylamino, but can also be, for example, methylethylamino, diethylamino, di-n-propylamino, diisopropylamino, or di-n-butylamino. Halogen is preferably Cl or Br, but can also be F or I.

Examples of esters of the penicillins of Formula I which can be readily hydrolyzed in vivo are those which are known from the penicillin literature to have this property. Such are, for instance, the acyloxymethyl esters, the ethoxycarbonyloxymethyl esters, the 1-ethoxycarbonyloxyethyl esters and the 3,4-benzo-2-oxotetrahydro-5-furyl esters.

Acyloxymethyl esters, particularly alkanoyloxymethyl esters in which alkanoyl is of up to 6 carbon atoms, and preferably the pivaloyloxymethyl esters, are preferred.

A penicillin of Formula I can be converted into an acid addition salt thereof by treatment with an acid. Preferred acids for this purpose are strong acids which form physiologically acceptable salts, for example, mineral acids, such as hydrochloric acid, hydrobromic acid, sulfuric acid or phosphoric acid, or strong organic carboxylic or sulfonic acids, such as formic acid, methanesulfonic acid, ethanesulfonic acid, benzenesulfonic acid, p-toluenesulfonic acid or 2-hydroxy-ethanesulfonic acid.

An acid of Formula I can also be converted into a metal or ammonium salt thereof by treatment with a base. The sodium and potassium salts of the new penicillins are obtained, for example, by dissolving a penicillin Formula I in the calculated quantity of dilute sodium hydroxide or potassium hydroxide solution and subsequently evaporating the solution. Salts with inorganic bases, such as diethylamine, triethylamine, diethanolamine, triethanolamine, N-ethyl-diethanolamine, pyrrolidine, piperidine, N-ethyl-piperidine, 1-(2- hydroxy-ethyl)-piperidine, morpholine, procaine, benzylamine, dibenzylamine and 1-phenylpropyl-2-amine can be obtained, for example, by reaction with the amine in an inert solvent, for example, dichloromethane. Alkali metal salts of the penicillins of Formula I can also be obtained by treating an alcoholic, preferably methanolic, solution of the penicillin with an alkali metal salt (for example, the K salt) of diethylacetic acid and precipitating the desired salt by adding an organic solvent, such as ether.

The compounds of Formula I are derivatives of ampicillin (Z = phenyl), amoxycillin (Z = p-hydroxyphenyl) and epicillin (Z = 1,4-cyclohexadienyl). The first mentioned derivatives are preferred, i.e., $R_1$ is preferably H. X is preferably O and Y is preferably H.

The $R_2$ and $R_3$ are preferably H or collectively are —CH=CH—CH=CH— or a corresponding group in which one CH group is replaced by N. Together with the pyridine ring, $R_2$ and $R_3$ collectively form a pyridine, quinoline or 1,5-, 1,6-, 1,7-, or 1,8-naphthyridine system which, apart from the substituted ureido group in the 3-position and the hydroxyl group in the 4-position, preferably has no further substituents. The $R_4$ radical is preferably $CH_3$, $OCH_3$, $N(CH_3)_2$ or Cl; the $R_5$ radical is preferably $CH_3$ or Cl. If $R_4$ and $R_5$ together form —CH=CH—CH=CH—, the system is a benzo[f]-quinoline, benzo[g]-quinoline, or benzo[h]-quinoline system. When $R_4$ and $R_5$ collectively form an aza-1,3-butadienyl group, the system is a phenanthroline or a pyrido-naphthyridine system. Of the phenathrolines, the 1,10-phenathrolines are preferred.

Preferred compounds of this invention are those compounds of Formula I in which at least one of the above radicals has one of the preferred values given above. Example of the preferred groups of compounds of this invention are those otherwise corresponding to Formula I but wherein:

Ia:
  X is O;
Ib:
  Z is phenyl;
Ic:
  Y is H;
Id:
  $R_2$ and $R_3$ each are H or together form —CH=CH—CH=CH—, —N=CH—CH=CH—, —CH=N—CH=CH—, —CH=CH—N=CH— or —CH=CH—CH=N—;
Ie:
  Y is H and $R_2$ and $R_3$ each are H or together form —CH=CH—CH=CH—;
If:
  $R_4$ is $CH_3$, $OCH_3$, $N(CH_3)_2$ or Cl,
  $R_5$ is $CH_3$ or Cl, or
  $R_4$ and $R_5$ together form —CH=CH—CH=N—;
Ig
  X is O,
  Y is H,
  Z is phenyl or p-hydroxyphenyl,
  $R_2$ and $R_3$ each are H or together form —CH=CH—CH=CH—, wherein one CH group may be replaced by N and/or 1 H atom may be replaced by $R_4$, and
  $R_4$ is $CH_3$, $C_2H_5$, $OCH_3$, $OC_2H_5$, Cl or Br;
Ih:
  X is O,
  Y is H,
  Z is phenyl,
  $R_2$ and $R_3$ each are H or together form —CH=CH—CH=CH—, wherein one CH group may be replaced by N and/or 1 H atom may be replaced by $R_4$, and
  $R_4$ is $CH_3$, $C_2H_5$, $OCH_3$, $OC_2H_5$, Cl or Br;
Ii:
  X is O,
  Y is H,
  Z is phenyl or p-hydroxyphenyl, and
  $R_2R_3$ each are H or together form —CH=CH—CH=CH—, —N=CH—CH=CH—, —CH=N—CH=CH—, —CH=CH—N=CH— or —CH=CH—CH=N—;
Ij:
  X is O,
  Y, $R_2$ and $R_3$ each are H, and
  Z is phenyl or p-hydroxyphenyl;
Ik:
  X is O,
  Y is H,
  Z is phenyl or p-hydroxyphenyl, and
  $R_2$ and $R_3$ together form —CH=CH—CH=CH—;
Il:
  X is O,
  Y is H,
  Z is phenyl, and
  $R_2$ and $R_3$ each are H or together form —CH=CH—CH=CH—, —CH=CH—N=CH— or —CH=CH—CH=N—;
Im:
  X is O,
  Y, $R_2$ and $R_3$ each are H, and
  Z is phenyl;
In:
  X is O,
  Y is H, and
  $R_2$ and $R_3$ each are H or together form —CH=CH—CH=CH—; and
Io:
  X is S,
  Y is H, and
  $R_2$ and $R_3$ each are H or together form —CH=CH—CH=CH—;

and the esters which can be readily hydrolyzed in vivo, especially alkanoyloxy methyl esters of up to 6 carbon atoms in the alkanoyl group, particularly the pivaloyloxymethyl esters, and the physiologically acceptable acid addition salts of these esters.

The compounds of Formula I have several centers of asymmetry, among which there is an asymmetric carbon atom in the phenylacetyl or cyclohexadienylacetyl group. The designations "D", "L" and "DL" refer to this center of asymmetry. The compounds of Formula I thus includes both the racemates and the optionally active isomers. The D-forms, derived from ampicillin, pivampicillin, amoxycillin and epicillin, of the compounds of Formula I and of groups Ia to Io are preferred.

In a process aspect, this invention relates to a process for the preparation of the novel penicillins of this invention which comprises:

i. reacting a penicillin of Formula II:

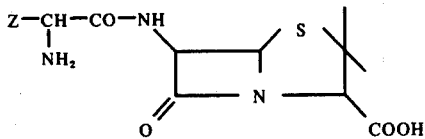

wherein Z has the values above-given, or a functional derivative thereof, with a compound of Formula III:

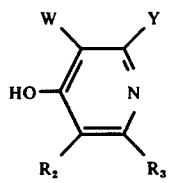

wherein W is —NH—COOH or —NCS and Y, and $R_2$ and $R_3$ have the values given above, or with a functional derivative thereof, or ii. reacting 6-aminopenicillanic acid, or a functional derivative thereof, with a compound of Formula IV:

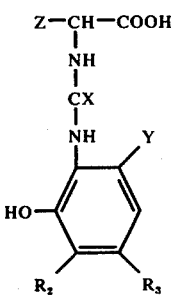

wherein X, Y, Z, $R_2$ and $R_3$ have the values given above, or with a functional derivative thereof, or iii. treating a compound which otherwise corresponds to Formula I but wherein at least one functional group is present in a functionally modified form, with a solvolyzing or hydrogenolyzing agent.

A carboxylic acid of Formula I obtained by any of the foregoing processes can, if desired, be esterified to form an ester which can be readily hydrolyzed in vivo and/or a resulting compound of Formula I can be converted by treatment with an acid or base into a physiologically acceptable salt thereof.

When the preparation of the compounds of Formula I (X=O) by reacting the starting materials of Formulae II and III (W=—NH—COOH) (or their functional derivatives) is novel and the synthesis of ureas from the corresponding amino compounds and carbamic acid derivatives of Formula III has not hitherto been described in the literature. In other respects, the preparation of the compounds of Formula I is carried out by methods which are in themselves known and are described in the literature (for example, in the standard work Houben-Weyl, *Methoden der Organischen Chemie* ("Methods of Organic Chemistry"), Georg-Thieme-Verlag, Stuttgart) and, particularly, in the literature relating to the synthesis of penicillins. The processes used are, in particular, suitably carried out under the reaction conditions which are known and suitable for the reactions in question.

All the starting materials for the preparation of the compounds of Formula I can, if desired, be formed in situ, in such a way that they are not isolated from the reaction mixture, but are immediately reacted further to form the compounds of Formula I. This is particularly the case for the unstable carbamic acids of Formula III and their derivatives.

Preferred derivatives of the starting materials of Formulae II and III, 6-aminopenicillanic acid (APA) and Formula IV which can be used in the preparation of the penicillins of Formula I, are reactive derivatives. The penicillanic acids of Formula II and APA can also be introduced into the reaction in the form of their esters which can be readily hydrolyzed in vivo. The carboxylic acids of Formula II, APA and of Formula IV can, for example, be used in the form of their salts, for example, in the form of their sodium, potassium or triethylamine salts, or in the form of their esters which can be readily hydrolyzed, for example, their trialkylsilyl esters (wherein the alkyl group preferably is of up to 4 carbon atoms). In addition, the amino derivatives of Formula II and APA can be used in the form of their N-trialkylsilyl derivatives (wherein each alkyl group preferably is of up to 4 carbon atoms), and the carbamic acids of Formula III (W = —NH—COOH) can preferably be used in the form of their "lactones", i.e., 2,3-dihydro-oxazolo [4,5-c] pyridin-2-ones of Formula V:

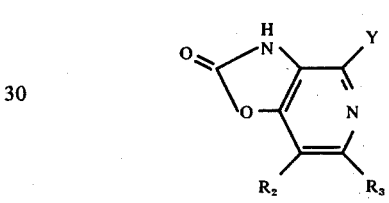

wherein Y, $R_2$ and $R_3$ have the values given above.

Suitable functional derivatives of the acids of Formula IV are, in particular, halides, preferably chlorides or bromines, anhydrides and mixed anhydrides, as well as azides and activated esters, for example, p-nitrophenyl esters, p-nitrophenyl thioesters or cyanomethyl esters. Examples of suitable mixed anhydrides of the acids of Formula IV are, on the one hand, those with lower alkanoic acids, particularly with acetic and substituted acetic acids, for example, pivalic acid, and, on the other hand, anhydrides with carbonic acids half-esters, such as can be obtained, for example, by reacting acids of Formula IV with chloroformic acid benzyl ester, p-nitrobenzyl ester, isobutyl ester, ethyl ester or allyl ester.

The starting materials of Formula II (ampicillin, amoxycillin and epicillin and their esters which can be readily hydrolyzed in vivo, such as pivampicillin, and the corresponding racemates and optically active isomers) are known. The starting materials of Formula III and their derivatives, particularly their "lactones", defined in greater detail above, have not hitherto been described in the literature. The "lactones" are readily accessible by reacting the corresponding 3-amino-4-hydroxypyridines, 3-amino-4-hydroxy-quinolines, 3-amino-4-hydroxy-naphthyridines or the correspondingly substituted benzo-quinolines, phenanthrolines or pyridonaphthyridines, with phosgene in pyridine. The isothiocyanates of Formula III (W = —NCS) can be prepared analogously with thiophosgene.

The compounds of Formula IV can be prepared by reacting the compounds of Formula III or their "lactones" with α-aminophenylacetic acid, α-amino-p- hydroxyphenylacetic acid or α-amino-1,4-cyclohexadienylacetic acid. The starting materials for the process according to the invention involving solvolysis or hydrogenolysis can be obtained analogously, but additional functional groups are present in the molecule.

The compounds of Formula I are preferably prepared by reacting the compounds of Formulae II and III or their functional derivatives. This reaction is preferably carried out in the presence of at least one inert solvent and at a temperature of from −20° to +35° C., preferably from 0° to 25° C. Suitable inert solvents are, for example, chlorinated hydrocarbons, such as dichloromethane (which is preferred), chloroform, 1,2-dichloroethane, trichloroethylene and tetrachloromethane; ethers, such as tetrahydrofuran and dioxane; ketones, such as acetone; amides, such as dimethylformamide (DMF); sulfoxides, such as dimethylsulfoxide; and nitriles, such as acetonitrile. If the starting material of Formula II is employed in the form of a salt, it is preferable to form the salt in situ by means of the corresponding base, for example, triethylamine, pyridine or aqueous sodium hydroxide solution. In this case, an excess of the base can also act as the solvent.

The compounds of Formula I can also be prepared by reacting APA (or its salts or esters) with an acid of Formula IV (or with a functional derivative thereof). This reaction is also preferably carried out in the presence of at least one of the inert solvents mentioned and in the temperature range indicated. If a salt of APA is employed, an excess of the base, such as triethylamine, pyridine or aqueous sodium hydroxide solution, used for the formation of this salt can also be used as the solvent.

APA or (preferably) an ester of APA which can be readily hydrolyzed in vivo can also be reacted with an acid of Formula IV in the presence of an agent which removes water, for example, a carbodiimide, such as dicyclohexylcarbodiimide, to form a compound of Formula I of (preferably) an ester thereof which can be readily hydrolyzed in vivo, preferably in the presence of at least one of the inert solvents mentioned and in the temperature range indicated.

The penicillins of Formula I can also be obtained by treating a compound which in other respects corresponds to Formula I, but in which at least one functional group is present in a functionally modified form, with a solvolyzing or hydrogenolyzing agent.

Examples of functionally modified groups which can be split off by solvolysis, preferably by hydrolysis, are esters which can be readily hydrolyzed, for example, the trimethylsilyl esters of the compounds of Formula I. Solvolysis is preferably carried out under very mild conditions in order not to endanger the other groups which can be hydrolyzed by solvolysis and which are present in the molecule. In general, the reaction is carried out in an aqueous or partially aqueous medium at a pH of from 3 to 10 and at a temperature of from 0° to 30° C., preferably 15° to 30° C. The trimethylsilyl esters mentioned can, for example, by hydrolyzed even with water or an alcohol, such as methanol or ethanol, at room temperature.

Examples of derivatives of the compounds of Formula I which can be split by hydrogenolysis, are the benzyl esters and the benzyl ethers. Hydrogenolysis can be carried out, for example, by treatment with hydrogen in the presence of a heavy metal catalyst, preferably a noble metal catalyst, such as platinum or palladium, at a temperature of from 0° to 30° C., preferably at room temperature, and at a pressure of from 1 to 100, preferably from 1 to 5, atmospheres in the presence of an inert solvent, for example, an alcohol, such as methanol or ethanol, an ether, such as tetrahydrofuran or dioxane, or a carboxylic acid, such as acetic acid. The reaction time is generally from 10 minutes to 2 hours.

A carboxylic acid of Formula I obtained by any of these processes can, if desired, be converted, by reaction with an esterifying agent, into an ester which can be readily hydrolyzed in vivo. For example, a salt, for example, a triethylamine salt, of a carboxylic acid of Formula I may be converted into the corresponding acyloxymethyl ester by reaction with an acyloxymethyl halide (wherein the acyl group is of up to 6 carbon atoms), for example, pivaloyloxymethyl chloride. This esterification is preferably carried out in the presence of one or more inert solvents at a temperature of from 0° to 30° C., preferably at room temperature. The use of a mixture of a halogenated hydrocarbon, such as dichloromethane, and DMF as the solvent is particularly preferred.

The novel penicillins of this invention can be used as medicaments in human or veterinary medicine in admixture with solid, liquid and/or semi-liquid inert, physiologically acceptable carriers or excipients. Suitable carriers are organic or inorganic substances which are suitable for enteral or parenteral administration or topical application and which do not react with the new compounds, for example, water, vegetable oils, benzyl alcohol, polyethylene glycols, gelatine, carbohydrates, such as lactose or starch, magnesium stearate, talc, petroleum jelly or cholesterol. Compositions in the form of tablets, dragees, capsules, syrups, elixirs, drops or suppositories are suitable for enteral administration and compositions in the form of solutions, preferably oily or aqueous solutions, or suspensions, emulsions or implants are suitable for parenteral administration; ointments, creams or powders are used for topical application. The new compounds can also be lyophilized and the lyophilizates obtained can be used in the manufacture of compositions for injection. Such composition can, if desired, be sterilized and/or contain adjuvants, such as lubricants, preservatives, stabilizers and/or wetting agents, emulsifiers, salts for controlling the osmotic pressure, buffer substances, colorants, flavorings and/or aroma substances. If desired, such compositions can also contain other active compounds, for example, other antibiotics (such as phenoxymethylpenicillin or cloxacillin, or aminoglycoside antibiotics, such as gentamycin, tobramycin or amikacin), in order to broaden the spectrum of action, antiphlogistics, antimycotics and/or vitamins. Solutions which are administered by intramuscular injection can, for example, additionally contain analgesics.

In general, the compounds according to the invention are administered analogously to the known compounds ampicillin, carbenicillin or pivampicillin. The daily dosage is preferably from 0.2 to 100 mg/kg of body weight. However, the appropriate specific dose for each particular patient depends on diverse factors, for example, on the effectiveness of the particular compound employed, on the age, the body weight, the general state of health, the sex, and the diet of the patient, the time and mode of administration, the rate of excretion, the medicament combination and the severity of the particular illness to which the therapy relates. Parental administration is preferred.

When the compounds according to the invention are formulated in dosage unit form, each dosage unit preferably contains from 10 to 5000 mg, more preferably 100 to 1000 mg, of the compound(s).

Each of the compounds of Formula I mentioned in the examples which follow is particularly suitable for the production of pharmaceutical preparations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In these examples, all temperatures are in °C.; the infrared spectra ("IR") are recorded in KBr. The $R_f$ values were determined on silica gel using dioxane-water 85:15; the spots are developed by spraying with an aqueous solution of potassium iodide and hydrogen hexachloroplatinate (IV) ("iodine plateate"). DMF is dimethylformamide and DMSO is dimethylsulfoxide. The compounds with a free COOH group are, in general, obtained in a hydrated form, mostly as dihydrates, and less often as trihydrates.

EXAMPLE 1 a. 3.5 g of ampicillin ($R_f$ 0.35) are dissolved in 50 ml. of dichloromethane and 10 ml. of triethylamine and 1.13 g. of crude 2,3-dihydro-oxazolo-[4,5-c]pyridin-2-one (obtainable by reacting 3-amino-4-hydroxypyridine with phosgene in pyridine) are then added. The mixture is stirred for 1 hour at 20° and is then extracted with 65 ml. of water. It is washed repeatedly with dichloromethane and dilute hydrochloric acid is added until the pH is 2. The crude precipitated D-α-(4-hydroxy-3-pyridyl-3-ureido)-benzylpenicillin (3,3-dimethyl-6-[1,4,6-triaza-2,5-dioxo-3-phenyl-6-(4-hydroxy-3-pyridyl)-hexyl]-7-oxo-4-thia-1-aza-bicyclo-[3,2,0]-heptane-2carboxylic acid) is filtered off and dried in air. IR 3,350, 3,000, 1,785, 1,738 and 1,678 cm$^{-1}$; $R_f$ 0.38.

Analogously, using:

2,3-dihydro-oxazolo-[4,5-c]-quinolin-2-one (obtainable from 3-amino-4-hydroxyquinoline and phosgene);
4-methyl-2,3-dihydro-oxazolo-[4,5-c]-quinolin-2-one;
4-n-butyl-2,3-dihydro-oxazolo-[4,5-c]-quinolin-2-one;
9-methyl-2,3-dihydro-oxazolo-[4,5-c]-quinolin-2-one;
9-ethyl-2,3-dihydro-oxazolo-[4,5-c]-quinolin-2one;
9-methoxy-2,3-dihydro-oxazolo-[4,5-c]-quinolin-2-one;
9-ethoxy-2,3-dihydro-oxazolo [4,5-c]-quinolin-2-one;
9-chloro-2,3-dihydro-oxazolo-[4,5-c]-quinolin-2-one;
9-bromo-2,3-dihydro-oxazolo-[4,5-c]-quinolin-2-one;
8-methyl-2,3-dihydro-oxazolo-[4,5-c]-quinolin-2-one;
8-ethyl-2,3-dihydro-oxazolo-[4,5-c]-quinolin-2-one;
8-methoxy-2,3-dihydro-oxazolo-[4,5-c]-quinolin-2one;
8-ethoxy-2,3-dihydro-oxazolo-[4,5-c]-quinolin-2-one;
8-chloro-2,3-dihydro-oxazolo-[4,5-c]-quinolin-2-one;
8-bromo-2,3-dihydro-oxazolo-[4,5-c]-quinolin-2-one;
8-dimethylamino-2,3-dihydro-oxazolo-[4,5-c]-quinolin-2-one;
8-diethylamino-2,3-dihydro-oxazolo-[4,5-c]-quinolin-2-one;
7-methyl-2,3-dihydro-oxazolo-[4,5-c]-quinolin-2-one;
7-ethyl-2,3-dihydro-oxazolo-[4,5-c]-quinolin-2-one;
7-isobutyl-2,3-dihydro-oxazolo-[4,5-c]-quinolin-2-one; 7-methoxy-2,3-dihydro-oxazolo-[4,5-c]-quinolin-2-one;
7-ethoxy-2,3-dihydro-oxazolo-[4,5-c]-quinolin-2-one;
7-fluoro-2,3-dihydro-oxazolo-[4,5-c]-quinolin-2-one;
7-chloro-2,3-dihydro-oxazolo-[4,5-c]-quinolin-2-one;
7-bromo-2,3-dihydro-oxazolo-[4,5-c]-quinolin-2-one;
7-iodo-2,3-dihydro-oxazolo-[4,5-c]-quinolin-2-one;
6-methyl-2,3-dihydro-oxazolo-[4,5-c]-quinolin-2-one;
6-ethyl-2,3-dihydro-oxazolo-[4,5-c]-quinolin-2-one;
6-methoxy-2,3-dihydro-oxazolo-[4,5-c]-quinolin-2-one;
6-ethoxy-2,3-dihydro-oxazolo-[4,5-c]-quinolin-2-one;
6-chloro-2,3-dihydro-oxazolo-[4,5-c]-quinolin-2-one;
6-bromo-2,3-dihydro-oxazolo-[4,5-c]-quinolin-2-one;
7,8-dimethyl-2,3-dihydro-oxazolo-[4,5-c]-quinolin-2-one;
7,8-dichloro-2,3-dihydro-oxazolo-[4,5-c]-quinolin-2-one;
7-chloro-8-methyl-2,3-dihydro-oxazolo-[4,5-c]-quinolin-2-one;
2,3-dihydro-oxazolo-[4,5-c]-1,5-naphthyridin-2-one (obtainable from 3-amino-4-hydroxy-2,5-naphthyridine and phosgene);
6-methyl-2,3-dihydro-oxazolo-[4,5-c]-1,5-naphthyridin-2-one;
6-ethyl-2,3-dihydro-oxazolo-[4,5-c]-1,5-naphthyridin-2-one;
6-methoxy-2,3-dihydro-oxazolo-[4,5-c]-1,5-naphthyridin-2-one;
6-ethoxy-2,3-dihydro-oxazolo-[4,5-c]-1,5-naphthyridin-2-one;
2,3-dihydro-oxazolo-[4,5-c]-1,6-naphthyridin-2-one;
6-methyl-2,3-dihydro-oxazolo-[4,5-c]-1,6-naphthyridin-2-one;
6-methoxy-2,3-dihydro-oxazolo-[4,5-c]-1,6-naphthyridin-2-one;
6-chloro-2,3-dihydro-oxazolo-[4,5-c]-1,6-naphthyridin-2-one;
6-bromo-2,3-dihydro-oxazolo-[4,5-c]-1,6-naphthyridin-2-one;
2,3-dihydro-oxazolo-[4,5-c]-1,7-naphthyridin-2-one;
6-chloro-2,3-dihydro-oxazolo-[4,5-c]-1,7-naphthyridin 2-one;
6-bromo-2,3-dihydro-oxoazolo-[4,5-c]-1,7-naphthyridin-2-one;
2,3-dihydro-oxazolo-[4,5-c]-1,8-naphthyridin-2-one;
7-methyl-2,3-dihydro-oxazolo-[4,5-c]-1,8-naphthyridin-2-one;

2,3-dihydro-oxazolo-[4,5-c]-benzo[g]-quinolin-2-one; and 2,3-dihydro-oxazolo-[4,5-c]-1,10-phenanthrolin-2-one, the following compounds are obtained by reaction with ampicillin:

D-α-(-hydroxy-3-quinolyl-3-ureido)-benzylpenicillin,
IR: 3,350, 3,000, 1,780, 1,738 and 1,670 cm$^{-1}$; $R_f$: 0.52;

D-α-(2-methyl-4-hydroxy-3-quinolyl-3-ureido)-benzylpenicillin,
IR: 3,300, 2,990, 1,778, 1,730 and 1,655 cm$^{-1}$; $R_f$: 0.44;

D-α-(2-n-butyl-4-hydroxy-3-quniolyl-3-uredio)-benzylpenicillin;

D-α-(4-hydroxy-5-methyl-3-quinolyl-3-uredio)-benzylpenicillin;

D-α-(4-hydroxy-5-ethyl-3-quinolyl-3-ureido)-benzylpenicillin;

D-α-(4-hydroxy-5-methoxy-3-quinolyl-3-ureido)-benzylpenicillin;

D-α-(4-hydroxy-5-ethoxy-3-quinolyl-3-ureido)-benzylpenicillin;

D-α-(4-hydroxy-5-chloro-3-quinolyl-3-ureido)-benzylpenicillin;

D-α-(4-hydroxy-5-bromo-3-quinolyl-3-ureido)-benzylpenicillin;

D-α-(4-hydroxy-6-methyl-3-quinolyl-3-ureido)-benzylpenicillin,
IR: 3,400, 2,980, 1,765, 1,725 and 1,660 cm$^{-1}$; $R_f$: 0.52;

D-α-(4-hydroxy-6-ethyl-3-quinolyl-3-ureido)-benzylpenicillin;

D-α-(4-hydroxy-6-methoxy-3-quinolyl-3-ureido)-benzylpenicillin;

D-α-(4-hydroxy-6-ethoxy-3-quinolyl-3-ureido)-benzylpenicillin;

D-α-(4-hydroxy-6-chloro-3-quinolyl-3-ureido)-benzylpenicillin, IR: 3,300, 2,950, 1,779, 1,722 and 1,660 cm$^{-1}$; $R_f$: 0.55;

D-α-(4-hydroxy-6-bromo-3-quinolyl-3-ureido)-benzylpenicillin, IR: 3,300, 2,980, 1,780, 1,735 and 1,660 cm$^{-1}$; $R_f$: 0.57;

D-α-(4-hydroxy-6-dimethylamino-3-quinolyl-3-ureido)-benzylpenicillin;

D-α-(4-hydroxy-6-diethylamino-3-quinolyl-3-ureido)-benzylpenicillin;

D-α-(4-hydroxy-7-methyl-3-quinolyl-3-ureido)-benzylpenicillin, IR: 3,300, 3,000, 1,780, 1730 and 1,670 cm$^{-1}$; $R_f$: 0.50;

D-α-(4-hydroxy-7-ethyl-3-quinooyl-3-ureido)-benzylpenicillin, IR: 3,300, 2,980, 1,778, 1740 and 1,660 cm$^{-1}$; $R_f$: 0.55;

D-α-(4-hydroxy-7-isobutyl-3-quinolyl-3ureido)-benzylpencillin;

D-α-(4-hydroxy-7-methoxy-3-quinolyl-3-ureido)-benzylpenicillin, IR: 3,350, 3,020, 1,782, 1,730 and 1,660 cm.$^{-1}$; $R_f$: 0.52;

D-α-(4-hydroxy-7-ethoxy-3-quinolyl-3-ureido)-benzylpenicillin, IR: 3,300, 2,970, 1776, 1,728 and 1,660 cm$^{-1}$; $R_f$: 0.53;

D-α-(4-hydroxy-7-fluoro-3-quinolyl-3-ureido)-benzylpenicillin;

D-α-(4-hydroxy-6-chloro-3-quinolyl-3-ureido)-benzylpenicillin, IR: 3,270, 2,960, 1,775, 1,721 and 1,658 cm$^{-1}$; $R_f$: 0.54;

D-α-(4-hydroxy-7-bromo-3-quinolyl-3-ureido)-benzylpenicillin;

D-α-(4-hydroxy-8-methyl-3-quinolyl-3-ureido)-benzylpencillin;

D-α-(4-hydroxy-8-ethyl-3-quinolyl-3-ureido)-benzylpenicillin;

D-α-(4-hydroxy-8-methoxy-3-quinolyl-3-ureido)-benzylpenicillin;

D-α(4-hydroxy-8-ethoxy-3-quinolyl-3-ureido)-benzylpenicillin;

D-α-(4-hydroxy-8-chloro-3-quinolyl-3-ureido)-benzylpencillin, IR: 3,320, 2,990, 1,774, 1,722 and 1,660 cm$^{-1}$; $R_f$: 0.57;

D-α-(4-hydroxy-8-bromo-3-quinolyl-3-ureido)-benzylpenicillin;

D-α-(4-hydroxy-6,7-dimethyl-3-quinolyl-3-ureido)-benzylpenicillin, IR: 3,320, 2,980, 1,750, 1,720 and 1,660 cm$^{-1}$; $R_f$: 0.53;

D-α-(4-hydroxy-6,7-dichloro-3-quinolyl-3-ureido)-benzylpenicillin, IR: 3,350, 2,980, 1,770, 1,718 and 1,640 cm$^{-1}$; $R_f$: 0.56;

D-α-(4-hydroxy-6-methyl-7-chloro-3-quinolyl-3-ureido)-benzylpenicillin, IR: 3,400, 2,970, 1,785, 1,735 and 1,665 cm$^{-1}$; $R_f$: 0.56;

D-α-[4-hydroxy-3-(1,5-naphthyridyl)-3-ureido]-benzylpenicillin, IR: 3,300, 2,980, 1,777, 1,725 and 1,660 cm$^{-1}$; $R_f$: 0.60 (in dioxane-water, 70:30);

D-α[4-hydroxy-8-methyl-3-(1,5-naphthyridyl)-3-ureido]-benzylpenicillin;

D-α-[4-hydroxy-8-ethyl-3-(1,5-naphthyridyl)-3-ureido]-benzylpenicillin;

D-α-[4-hydroxy-8-methoxy-3-(1.5-naphthyridyl)-3-ureido]-benzylpenicillin;

D-α-[4-hydroxy-8-ethoxy-3-(1,5-naphthyridyl)-3-ureido]-benzylpenicillin;

D-α-[4-hydroxy-3-(1,6-naphthyridyl)-3-ureido]-benzylpenicillin, IR: 3,330, 2,970, 1,780, 1,724 and 1,645 cm$^{-1}$; $R_f$: 0.43;

D-α-[4-hydroxy-8-methyl-3-(1.6-naphthyridyl)-3-ureido]-benzylpenicillin;

D-α-[4-hydroxy-8 methoxy-3-(1,6-naphthyridyl)-3-ureido]-benzylpenicillin;

D-α-[4-hydroxy-8-chloro-3-(1,6-naphthyridyl)-3-ureido]-benzylpenicillin;

D-α-[4-hydroxy-8-bromo-3-(1,6-naphthrydidyl)-3-ureido]-benzylpenicillin;

D-α[4-hydroxy-3-(1,7-naphtrhyridyl)-3-benzylpencillin,, IR: 3,350, 2,960, 1,775, 1,730 and 1,658 cm$^{-1}$; $R_f$: 0.45;

D-α-[4-hydroxy-8-chloro-3-(1,7-naphthyridyl)-3-ureido]-benzylpencillin;

D-α-[4-hydroxy-8-bromo-3-(1,7-naphthyridyl)-3ureido]-benzylpencillin;

D-α[-4-hydroxy-3-(1,9-naphthridyl)-3-ureido]-benzylpenicillin, IR: 3,300, 2,950, 1,780, 1,728 and 1,660 cm$^{-1}$; $R_f$: 0.48;

D-α-[4-hydroxy-7-methyl-3-(1,8-naphthylridyl)-3-ureido]-benzylpenicillin;

D-α[4-hydroxy-3-(benzyl[g]quinolyl)-3-ureido]-benzylpencillin; and

D-α-[4-hydroxy-3(1.10-phenanthrolyl)-3-ureido]-benzylpencillin, IR: 3,320, 2,960, 1,775, 1,725 and 1,663 ch$^{-1}$; $R_f$: 0.50.

b. 1g. of D-α-(4-hydroxy-3-pyridyl-3-ureido)-benzylpencillin is dissolved in 5 ml. of dichloromethane and 5 ml. of triethylamine and the mixture is evaporated at 20°–25° to give the corresponding triethylamine salt.

EXAMPLE 2

5 g. of pivampicillin hydrochloride (R$_f$: 0.72) are dissolved in a mixture of 100 ml. of dichloromethane and 3 ml. of triethylamine and a solution of 1.72 g. of 2,3-dihydro-oxazolo[4,5-c]-pyridin-2-one in 40 ml. of DMF and 40 ml. of DMSO is added. After stirring for one hour at 20°, the mixture is filtered and the solution is washed with very dilute hydrochloric acid (pH 2–3) and is dried over sodium sulfate. After filtration and evaporation, D--α(4-hydroxy-3-pyridyl-3-ureido)-benzylpenicillin privaloyloxylmethyl ester is obtained, m.p. 161°–164°; IR: 3,280, 3,000, 1,785, 1,760 and 1,675 cm$^{-1}$; R$_f$: 0.66.

The following are obtained analogously from pviampicillin hydrochloride and the corresponding cyclic carbamates mentioned in Example 1:

D-α-(4-Hydroxy-3-quinolyl-3-ureido)-benzylpenicillin pivaloyloxymethyl ester, IR: 3,300, 2,980, 1,748, 1,760 and 1,662 cm$^{-1}$; R$_f$: 0.77;

D-α-(2-methyl-4-hydroxy-3-quinolyl-3-ureido)-benzylpencillin pivaloyloxymethyl ester, IR: 3,300, 2,980, 1,780, 1,760 and 1,660 cm$^{-1}$; R$_f$: 0.74;

D-α-(4-hydroxy-5-methyl-3-quinolyl-3-ureido)-benzylpencillin pivaloxyloxymethyl ester;

D-α-(4-hydroxy-5-ethyl-3-quinolyl-3-ureido)-benzylpencillin povaloxyloxymethyl ester;

D-α-(4-hydroxy-5-methoxy-3-quinoly-3-ureido)-benzylpencillin pivaloyloxymethyl ester;

D-α-(4-hydroxy-5-ethoxy-3-quinolyl3-ureido)-benzylpencillin pivaloyloxmethyl ester;

D-α(4-hydroxy-5-choro-1-quinolyl-3-ureido)-benzylpencillin pivaloyoloxymethyl ester;

D-α-(4-hydroxy-5-bromo-3-quiniolyl-3-ureido)-benzylpencillin pviloyloxymethyl ester;

D-α(4-hydroxy-6-methyl-3-quinolyl-3-ureido)-benzylpencillin pivloyloxymethyl ester, IR: 3,300, 2,980, 1,780, 1,760 and 1662 cm$^{-1}$; R$_f$: 0,80;

D-α(4-hydroxy-6-ethyl-3-quinolyl-3uriedo)-benzylpencillin pivoaloyloxymethyl ester;

D-α-(4-hydroxy-6-methoxy-3-quinolyl-3-ureido)-benzylpencillin pivaloyloxymethyl ester;

D-α-(4-hydroxy-6-ethoxy-3-quinolyl-3ureido)-benzylpencillin pivaloxyloxymethyl ester;

D-α-(4-hydroxy-6-chloro-3-quinolyl-3-ureido)-benzylpencillin pivaloyloxymethyl ester;

D-α-(4-hydroxy-6-bromo-3-quinolyl-3-ureido)-benzylpencillin pivaloyloxmethyl ester, IR: 1,330, 3,005, 1,780, 1,760 and 1,660 cm$^{-1}$; R$_f$: 0.79;

D-α-(;b 4-hydroxy-6-dimethylamino-3quinolyl-3-ureido)-benzylpencillin pivaloxyloxymethyl ester;

D-α-(4-hydroxy-7-methyl-3-quinolyl-3-ureido)-benzylpencillin pvialoyloxymethyl ester, IR: ;b 3,380, 3,000, 1,788, 1,763 and 1,682 cm$^{-1}$; R$_f$: 0.77;

D-α-(4-hydroxy-7-ethyl-3-quinolyl-3-ureido)-benzylpencillin pivaloyloxymethyl ester, IR: 3,300, 2.980, 1,785, 1,760 and 1,678 cm$^{-1}$; R$_f$: 0.80;

D-α-(4-hydroxy-7-methoxy-3-quinolyl-3-ureido)-benzylpencillin pivaloyloxymethyl ester, IR: 3,350, 3,020, 1,790, 1,762 and 1,670 cm$^{-1}$; R$_f$: 0.78;

D-α-(4-hydroxy-7-ethoxy-3-quinolyl-3-ureido)-benzylpencillin pivaloyloxymethyl ester, IR: 3,300, 2,980, 1,780, 1,756 and 1,680 cm$^{-1}$; R$_f$: 0.78;

D-α(4-hydroxy-7-chloro-3-quinolyl-3-ureido)-benzylpencillin pivaloyloxymethyl ester, IR: 3,280, 2,970, 1,782, 1,756 and 1,666 cm$^{-1}$; R$_f$: 0.79;

D-α-(4-hydroxy-7-bromo-3-quinolyl-3-ureido)-benzylpenicillin pivaloyloxymethyl ester;

D- α-(4-hydroxy-8-methyl-3-quinolyl-3-ureido)-benzylpenicillin pivaloyloxymethyl ester;

D-α-(4-hydroxy-8-ethyl-3-quinolyl-;b 3ureido)-benzylpenicillin pivloyloxymethyl ester;

D-α-(4-hydroxy-8-methoxy-3-quinolyl-3-ureido)-benzylpenicillin pivaloxyloxymethyl ester;

D-α-(4-hydroxyk-8-ethoxy-3-quinolyl-3-ureido)-benzylpenicillin pivaloyloxymethyl ester;

D-α-(4-hydroxy-8-chloro-3-quinolyl-3-ureido)-benzylpenicillin pivaloxyloxymethyl ester; IR: 3,310, 2,980, 1,782, 1,761 and 1,672 cm$^{-1}$; R$_f$: 0.82;

D-60-(4-hydroxy-8-bromo-3-quinolyl-3-ureido)-benzylpenicillin pivaloyloxymethyl ester;

D-α-(4-hydroxy-6,7-diemthyl-3-quiniolyl-3-ureido)-benzylpencillin pivaloxyloxymethy ester, IR: 3,300, 2,990, 1,780, 1,762 and 1,663 cm$^{;116\ 1}$; R$_f$: 0.80;

D-α-(4-hydroxy-l6,7-dichloror -3:quinolyl-3:urieod)-benzylpencillin pivaloyloxymethyl ester, IR: 3,320, 2,990, 1,775, 1,765 and 1,640 cm$^-$; R$_f$: 0.83;

D-α-(4-hydroxy-6-methyl-7-chloroj-3-quinolyl-3-ureido)-benzylpencillin pivaloyloxymethyl ester, IR: 3,310, 2,0990, 1,780, 1,762 and 1,665 cm$^{-1}$; R$_f$: 0.83;

D-α[4-hydroxy-3-(1,5-naphythryridyl)-3-ureido]-benzylpencillin pivaloyloxymethyl ester, IR: 3,350, 2,960, 1,780, 1,760 and 1,670 cm$^{-1}$; R$_f$: 0.83

D-α-[4:hydroxy-8-methyl-3-(1,5-naphthyridtyl)-3-ureido]-benzylpenicillin pivaloyloxymelthyl ester;

D-α-[4-hydroxy-8-ethyl-3-(1,5-naphthyridyl)-3-ureido]-benzylpencillin pivaloyloxymethyl ester;

D-α[-4-hydroxy-8-methoxy-3-(,15-naphthyridyl)-3-ureido]-benzylpencillin pivaloyloxymethyl ester;

D-α-[4-hydroxy-8-ethoxy-3-(1,5-naphthyridyl)-3-ureido]-benzylpencillin pivaloyloxymethyl ester;

D-α-[4-hydroxy-3-(1,6-naphthridyl)-3-ureido]-benzylpenicillin pivaloyloxymelthyl ester, IR: 3,300, 2,990, 1,770, 1,760 and 1,660 cm$^{-1}$; R$_f$: 0.66 ( in dioxane-water, 70:30);

D-α-[4-hydroxyk-8-methyl-3-(1,6-naphthyridyl)-3-ureido]-benzylpenicillin pivaloxyloxymethyl ester;

D-α-[4-hydroxy-8-methoxy-3-(1,6-napthyridyl)-3-ureido]-benzylpenicillin pivaloyloxymethyl ester;

D-α-[4-hydroxy-8-chloro-3-(1,6-naphthyridyl)-3-ureido]-benzylpenicillin pivaloyloxmethyl ester;

D-α-[4-hydrocy-8-bromo-3-(1,6-napthyridyl)-3-ureido]-benzylpenicillin pivaloyloxymethyl ester;

D-α-[4-hydroxy-3-(1,7-naphthyridyl)-3-ureido]-benzylpenicillin pivoaloyoxymethyl ester, IR: 3,320, 2,990, 1,780, 1,758 and 1,660 cm$^{-1}$; R$_{fl}$: 0.71;

D-α-[4-hydroxy-8-chloro-3-(1,7-napthyridyl)-3-ureido]-benzylpenicillin pivaloyoloxymethyl ester;

D-60-[4-hydroxy-8-bromo-3-(1,7-napthyridyl)-3-ureido]-benzylpenicillin pivaloyloxymethyl ester;

D-α-[4-hydroxy-3-(1,8-napthyyridyl)-3-ureido]-benzylpenicillin pivaloymethyl ester, IR: 3,300, 2,980, 1,780, 1,760 and 1,665 cm$^{-1}$; R$_f$: 0,75;

D-α-[4-hydroxy-7-methyl-3-(1,8-napthyridyl)-3-ureido]-benzylpenicillin pivaloyloxymethyl ester; and D-α-[4-hydrxoy-3-(1,10-phenenthrolyl)-3-ureido]-benzylpneicillin pivaloyloxymethyl ester, IR: 3,330, 2,990, 1782, 1,760 and 1,670 cm$^{-1}$; R$_f$: 0.77.

EXAMPLE 3

D-α-[4-Hydroxy-3-pyridyl-3-ureido)-p-hydroxybenzylpenicillin; IR: potassium salt: 3,270, 3,000, 1,770, 1,665 and 1,600 cm$^{-1}$; $R_f$:0.41, is obtained, analogously to Example 1, from amoxycillin and 2,3-dihydro-oxazolo-[4,5-c]-pyridin-2-one.

The following are obtained analogously fro amoxycillin and the corresponding cyclic carbomate named in Example 1:

D-α-(4-hydroxy-3-quinolyl-3-ureido)-p-hydroxybenzylpeencillin,
IR: 3,300, 2,980, 1,770, 1,722 and 1,660 cm$^{-1}$; $R_f$: 0.54;

D-α-(2-methyl-4-hydroxyl-3-quinolyl--b 3-ureido-p-hydroxybenaylpenicillin, IR: 3,280, 2,980, 1,762, 1,730 and 1,640 cm$^{-1}$; $R_f$: 0.41;

D-α-[(4-hydroxy-5-methyl-3-quinolyl-3-ureido)-p-hydroxybenzylpenicillin;

D-α-(4-hydroxyl-5-ethyl-3-quinolyl-3-ureido)-p-hydroxybenzylpenicillin;

D-α-(4-hydroxyl-5-methoxy-3-quinolyl-3-ureido)-p-hydroxybenzylpenicillin;

D-α-(4-hydroxyl-5-ethoxy-3quinolyl-3-ureido)-p-hydroxybenzylpenicillin;

D-α-(4-hydroxyl-5-chloro-3-quinoly-3-ureido)-p-hydroxybenzlypenicillin;

D-α-(4-hydroxyl-5-bromo-3-quinolyl-3-ureido)-p-hydroxybenzylpenicillin;

D-α-(4-hydoxy-6-methyl-3-quinolyl-3-ureido)-p-hydroxylbenzylpenicillin, IR: 3,300, 2,990, 1,775, 1,720 and 1,660 cm$^{-1}$; $R_f$: 0,53;

D-α-(4-hydroxyl-6-ethyl-3-quinoly-3-uredo)-p-hydroxybenzylpenicillin;

D-α-(4-hydroxy-6-methoxy-3-quinolyl-3-ureido)-p-hyroxybenzylpenicillin;

D-α-(4-hydroxy-6-ethoxy-3-quinolyl-3-ureido)-p-hydroxybenzyl0enicillin;

D-α-(4-hydroxy-6-chloro-3-quinoly-3-ureido)-p-hydroxybenzylpenicillin; IR: 3,300, 2,970, 1,774, 1,722 and 1,658 cm$^{-1}$; $R_f$: 0.52; D-α-(4-hydroxyl-6-bromo-3-quinolyl-3ureido)-p-hydroxybenzylpenicillin, IR: 3,300, 2,990, 1,775, 1,725 and 1,660 cm$^{-1}$; $R_f$: 0.55;

D-α-(4-hydroxy-6-dimethylamino-3-quinolyl-3-ureido(-p-hydroxybenzylpenicillin;

D-α-(4-hydroxyl-7-methyl-3-quinolyl-3-ureido)-p-hydroxybenzylpencillin, IR: 3,330, 3,000, 1,776, 1,725, and 1,660 cm$^{-1}$; $R_f$: 0.54;

D-α-(4-hydroxy-7-l -ethyl-3-quinolyl-3-ureido)-p-hydroxybenzylpenicillin, IR: 3,330, 1,776, 1,725, and 1,660 cm$^{-1}$; $R_f$: 0.54;

D-α-(4-hydroxy-7-ethyl-3-quinolyl-3-ureido)-p-hydroxylbenzylpenicillin, IR: 3,300, 2,980, 1,780, 1,732 and 1,658 cm$^{-1}$; $R_f$: 0.54;

D-α-(4-hydroxyl-7-methoxy-3-quinolyl-3ureido)-p-hydroxylbenzylpenicillin, IR: 3,340, 3,020, 1,785, 1,730 and 1,665 cm$^{-1}$; $R_f$: 0.51;

D-α-(4-hydroxyl-7-ethoxy-3-quinolyl-3-ureido)-p-hydroxybenzylpenicillin, IR: 3,300, 2,960, 1,777, 1,725 and 1,658 cm$^{-1}$; $R_f$: 0.52;

D-α-(4-hydroxyl-7-chloro-3-quinolyl-3-ureido)-p-hydroxybenzylpenicillin, IR: 3,280, 2,980, 1,776, 1,725 and 1,655 cm$^{-1}$; $R_f$: 0.56;

D-α-(4-hydroxyl-7-bromo-3-quinolyl-3-ureido)-p-hydroxybenzylpenicillin;

D-α-(4-hydroxyl-8-methyl-3-quinolyl-3-ureido)-p-hydroxybenzylpenicillin;

D-α-(4-hydroxyl-8-ethyl-3quinolyl-3ureido)-p-hydroxybenzylpenicillin;

D-α-(4-hydroxy-8methoxy-3quinolyl-3-ureido)-p-hydroxybenzylpenicillin;

D-α-(4-hydroxy-8-ethoxy-3-quinolyl-3-ureido)-p-hydroxybenzylpenicillin;

D-α-(4-hydroxyl-8-chloro-3-quinolyl-3-ureido)-p-hydroxybenzylpenicillin, IR: 3,320, 2,980, 1,772, 1,722 and 1,660 cm$^{-1}$: $R_f$: 0.55;

D-α-(4-hydroxy-8-bromo-3-quinolyl-3-ureido)-p-hydroxybenzylpenicillin;

D-α-(4-hydroxy-6,7-dimethyl-3-quinolyl-3-ureido)-p-hydroxybenzylpenicillin, IR: 3,300, 2,990, 1,770, 1,720 and 1,640 cm$^{-1}$; $R_f$: 0.52;

D-α-(4-hydroxy-6,7-dichloro-3-quinolyl-3-ureido)-p-hydroxybenzylpenicillin, IR: 3,320, 2,980, 1,778, 1,722 and 1,660 cm$^{-1}$; $R_f$: 0.56;

D-α-(4-hydroxy-6-methyl-7-chloro-3-quinolyl-3-ureido)-p-hydroxybenzylpenicillin, IR: 3,380, 2,980, 1,775, 1,722 and 1,660 cm$^{-1}$; $R_f$: 0.56;

D-α-[4-hydroxy-3-(1,5-naphthyridyl)-3-ureido]-p-hydroxybenzylpenicillin, IR: 3,290, 2,960, 1,775, 1,723 and 1,655 cm$^{-1}$; $R_f$: 0.64 (in dioxane-water, 70:30);

D-α-[4-hydroxy-8-methyl-3-(1,5-naphthyridyl)-3-ureido]-p-hydroxybenzylpenicillin;

D-α-[4-hydroxy-8-ethyl-3-(1,5-naphthyridyl)-3-ureido]-p-hydroxybenzylpenicillin;

D-α-[4-hydroxy-8-methoxy-3-(1,5-naphthyridyl)-3-ureido]-p-hydroxybenzylpenicillin;

D-α-[4-hydroxy-8-ethoxy-3-(1,5-naphthyridyl)-3-ureido]-p-hydroxybenzylpenicillin; D-α-[4-hydroxy-3-(1,6-naphthyridyl)-3-uredio]-p-hydroxybenzylpenicillin, IR: 3,270, 2,960, 1,765, 1,730 and 1,640 cm$^{-1}$; $R_f$: 0.66 (in dioxane-water, 70:30);

D-α-[4-hydroxy-8-methyl-3-(1,6-naphthyridyl)-3-ureido]-p-hydroxybenzylpenicillin;

D-α-[4-hydroxy-8-methoxy-3-(1,6-naphthyridyl)-3-ureido]-p-hydroxybenzylpenicillin;

D-α-[4-hydroxy-8-chloro-3-(1,6-naphthyridyl)-3-ureido]-p-hydroxybenzylpenicillin;

D-α-[4-hydroxy-8-bromo-3-(1,6-naphthyridyl)-3-ureido]-p-hydroxybenzylpenicillin;

D-α[4-hydroxy-3(1,7-naphthyridyl)-3-ureido]-p-hydroxybenzylpenicillin, IR: 3,300, 2,970, 1,780, 1,740 and 1,663 cm$^{-1}$; $r_f$: 0.44;

D-α-[4-hydroxy-8-chloro-3-(1,7-naphthyridyl)-3-ureido]-p-hydroxybenzylpenicillin;

D-α-[4-hydroxy-8-bromo-3-(1,1-naphthyridyl)-3-uredio]-p-hydroxybenzylpenicillin;

D-α-[4-hydroxy-3-(1,8-naphthyridyl)-3-ureido]-p-hydroxybenzylpenicillin, IR: 3,300, 2,950, 1,768, 1,735 and 1,658 cm$^{-1}$; $R_f$: 0.46;

D-α-[4-hydroxy-7-methyl-3-(1,8-naphthyridyl)-3-ureido]-p-hydroxybenzylpenicillin; and D-α-[4-hydroxy-3-(1,10-phenanthrolyl)-3-ureido]-p-hydroxybenzylpenicillin, IR: 3,330, 2,980, 1,780, 1,735 and 1,660 cm$^{-1}$; $R_f$: 0.44.

EXAMPLE 4

D-α-(4-Hydroxy-3-pyridyl-3-ureido)-1,4-cyclohexadienylmethylpenicillin, IR: 3,360, 2,990, 1,780, 1,725 and 1,660 cm$^{-1}$; $R_f$: 0.37, is obtained, analogously to Example 1, from epicillin and 2,3-dihydro-oxazolo-[4,5-c]-pyridin-2-one.

The followng are obtained analogously from epicillin and the corresponding cyclic carbamates named in Example 1;

D-α-(4-hydroxy-3-quinolyl-3-ureido)-1,4-cyclohexadienylmethylpenicillin, IR: 3,320, 2,970, 1,780, 1,740 and 1,665 cm$^{-1}$; R$_f$: 0.54;

D-α-(2-methyl-4-hydroxy-3-quinolyl-3-ureido)-1,4-cyclohexadienylmethylpenicillin, IR: 3,300, 2,960, 1,781, 1,725 and 1,660 cm$^{-1}$; R$_f$: 0.45;

D-α-(4-hydroxy-5-methyl-3-quinolyl-3-ureido)-1,4-cyclohexadienylmethylpenicillin, D-α-(4-hydroxy-5-ethyl-3-quinolyl-3-ureido)-1,4-cyclohexadienylmethylpenicillin;

D-α-(4-hydroxy-5-methoxy-3-quinolyl-3-ureido)-1,4-cyclohexadienylmethylpenicillin;

D-α-(4-hydroxy-5-ethoxy-3-quinolyl-3-ureido)-1,4-cyclohexadienylmethylpenicillin;

D-α-(4-hydroxy-5-chloro-3-quinolyl-3-ureido)-1,4-cyclohexadienylmethylpenicillin;

D-α-(4-hydroxy-5-bromo-3-quinolyl-3-ureido)-1,4-cyclohexadienylmethylpenicillin;

D-α-(4-hydroxy-6-methyl-3-quinolyl-3-ureido)-1,4-cyclohexadienylmethylpenicillin, IR: 3,300, 2,970, 1,780, 1,725 and 1,658 cm$^{-1}$; R$_f$: 0.56; D-α-(4-hydroxy-6-ethyl-3-quinolyl-3-ureido)-1,4-cyclohexadienylmethylpenicillin;

D-α-(4-hydroxy-6-methoxy-3-quinolyl-3-ureido)-1,4-cyclohexadienylmethylpenicillin;

D-α-(4-hydroxy-6-ethoxy-3-quinolyl-3-ureido)-1,4-cyclohexadienylmethylpenicillin;

D-α-(4-hydroxy-6-chloro-3-quinolyl-3-ureido)-1,4-cyclohexadienylmethylpenicillin, IR: 3,300, 2,980, 1,780, 1,725 and 1,660 cm$^{-1}$; R$_f$: 0.56;

D-α-(4-hydroxy-6-bromo-3-quinolyl-3-ureido)-1,4-cyclohexadienylmethylpenicillin;

D-α-(4-hydroxy-6-dimethylamino-3-quinolyl-3-ureido)-1,4-cyclohexadienylmethylpenicillin;

D-α-(4-hydroxy-7-methyl-3-quinolyl-3-ureido)-1,4-cyclohexadienylmethylpenicillin;

D-α-(4-hydroxy-7-ethyl-3-quinolyl-3-ureido)-1,4-cyclohexadienylmethylpenicillin, IR: 3,290, 2,980, 1,780, 1,725 and 1,660 cm$^{-1}$; R$_f$: 0.55;

D-α-(4-hydroxy-7-methoxy-3-quinolyl-3-ureido)-1,4-cyclohexadienylmethylpenicillin;

D-α-(4-hydroxy-7-ethoxy-3-quinolyl-3-ureido)-1,4-cyclohexadienylmethylpenicillin, IR: 3,330, 2,980, 1,783, 1,735 and 1,665 cm$^{-1}$; R$_f$: 0.53;

D-α-(4-hydroxy-7-chloro-3-quinolyl-3-ureido)-1,4-cyclohexadienylmethylpenicillin;

D-α-(4-hydroxy-7-bromo-3-quinolyl-3-ureido)-1,4-cyclohexadienylmethylpenicillin;

D-α-(4-hydroxy-8-methyl-3-quinolyl-3-ureido)-1,4-cyclohexadienylmethylpenicillin;

D-α-(4-hydroxy-8-ethyl-3-quinolyl-3-ureido)-1,4-cyclohexadienylmethylpenicillin;

D-α-(4-hydroxy-8-methoxy-3-quinolyl-3-ureido)-1,4-cyclohexadienylmethylpenicillin;

D-α-(4-hydroxy-8-ethoxy-3-quinolyl-3-ureido)-1,4-cyclohexadienylmethylpenicillin;

D-α-(4-hydroxy-8-chloro-3-quinolyl-3-ureido)-1,4-cyclohexadienylmethylpenicillin;

D-α-(4-hydroxy-8-bromo-3-quinolyl-3-ureido)-1,4-cyclohexadienylmethylpenicillin;

D-α-(4-hydroxy-6,7-dimethyl-3-quinolyl-3-ureido)-1,4-cyclohexadienylmethylpenicillin, IR: 3,300, 2,980, 1,778, 1,725 and 1,660 cm$^{-1}$; R$_f$: 0.54;

D-α-(4-hydroxy-6,7-dichloro-3-quinolyl-3-ureido)-1,4-cyclohexadienylmethylpenicillin, IR: 3,300, 2,980, 1,780, 1,720 and 1,659 cm$^{-1}$; R$_f$: 0.58;

D-α-(4-hydroxy-6-methyl-7-chloro-3-quinolyl-3-ureido)-1,4-cyclohexadienylmethylpenicillin, IR: 3,330, 2,990, 1,782, 1,725 and 1,660 cm$^{-1}$; R$_f$: 0.56;

D-α-[4-hydroxy-3-(1,5-naphthyridyl)-3-ureido]-1,4-cyclohexadienylmethylpenicillin;

D-α-[4-hydroxy-8-methyl-3-(1,5-naphthyridyl)-3-ureido]-1,4-cyclohexadienylmethylpenicillin;

D-α-[4-hydroxy-8-ethyl-3-(1,5-naphthyridyl)-3-ureido]-1,4-cyclohexadienylmethylpenicillin;

D-α-[4-hydroxy-8-methoxy-3-(1,5-naphthyridyl)-3-ureido]-1,4-cyclohexadienylmethylpenicillin;

D-α-[4-hydroxy-8-ethoxy-3-(1,5-naphthyridyl)-3-ureido]-1,4-cyclohexadienylmethylpenicillin;

D-α-[4-hydroxy-3-(1,6-naphthyridyl)-3-ureido]-1,4-cyclohexadienylmethylpenicillin;

D-α-[4-hydroxy-8-methyl-3-(1,6-naphthyridyl)-3-ureido]-1,4-cyclohexadienylmethylpenicillin;

D-α-[4-hydroxy-8-methoxy-3-(1,6-naphthyridyl)-3-ureido]-1,4-cyclohexadienylmethylpenicillin;

D-α-[4-hydroxy-8-chloro-3-(1,6-naphthyridyl)-3-ureido]-1,4-cyclohexadienylmethylpenicillin;

D-α-[4-hydroxy-8-bromo-3-(1,6-naphthyridyl)-3-ureido]-1,4-cyclohexadienylmethylpenicillin;

D-α-[4-hydroxy-3-(1,7-naphthyridyl)-3-ureido]-1,4-cyclohexadienylmethylpenicillin, IR: 3,300, 2,980, 1,119, 1,725 and 1,660 cm$^{-1}$; R$_f$: 0.49;

D-α-[4-hydroxy-8-chloro-3-(1,7-naphthyridyl)-3-ureido]-1,4-cyclohexadienylmethylpenicillin;

D-α-[4-hydroxy-8-bromo-3-(1,7-naphthyridyl)-3-ureido]-1,4-cyclohexadienylmethylpenicillin;

D-α-[4-hydroxy-3-(1,8-naphthyridyl)-3-ureido]-1,4-cyclohexadienylmethylpenicillin;

D-α-[4-hydroxy-7-methyl-3-(1,8-naphthyridyl)-3-ureido]-1,4-cyclohexadienylmethylpenicillin; and D-α-[4-hydroxy-3-(1,10-phenanthrolyl)-3-ureido]-1,4-cyclohexadienylmethylpenicillin, IR: 3,320, 2,975, 1,782, 1,735 and 1,665 cm$^{-1}$; R$_f$: 0.47.

EXAMPLE 5

D-α-(4-Hydroxy-3-quinolyl-3-thioureido)-benzylpenicillin, IR: 3,310, 3,010, 1,770, 1,730 and 1,675 cm$^{-1}$; R$_f$: 0.50, is obtained, analogously to Example 1, from ampicillin and 4-hydroxyquinolyl-3-isothiocyanate (which can be prepared from 3-amino-4-hydroxyquinoline and thiophosgene in pyridine).

Analogously, 4-hydroxy-quinolyl-3-isothiocyanate with pivampicillin gives:

D-α-(4-hydroxy-3-quinolyl-3-thioureido)-benzylpenicillin pivaloyloxymethyl ester, IR: 3,350, 3,020, 1,780, 1,772 and 1,668 cm$^{-1}$; R$_f$: 0.78;

with amoxycillin gives:

D-α-(4-hydroxy-3-quinolyl-3-thioureido)-p-hydroxybenzylpenicillin, IR: 3,250, 2,930, 1,770, 1,720 and 1,665 cm$^{-1}$; R$_f$: 0.49; and with epicillin gives:

D-α-(4-hydroxy-3-quinolyl-3-thioureido)-1,4-cyclohexadienylmethylpenicillin, IR: 3,270, 2,970, 1,782, 1,735 and 1,663 cm$^{-1}$; R$_f$: 0.55.

Analogously, 4-hydroxy-pyridyl-3-isothiocyanate gives:

D-α-(4-hydroxy-3-pyridyl-3-thioureido)-benzylpenicillin;

D-α-(4-hydroxy-3-pyridyl-3-thioureido)-benzylpenicillin pivaloyloxymethyl ester;

D-α-(4-hydroxy-3-pyridyl-3-thioureido)-p-hydroxybenzylpenicillin; and

D-α-(4-hydroxy-3-pyridyl-3-thioureido)-1,4-cyclohexadienylmethylpenicillin.

EXAMPLE 6 a. 22.9 g. of phosphorus pentachloride are added to a suspension of 28.7 g. of DL-2-(4-hydroxy-3-pyridyl-3-ureido)-phenylacetic acid (obtainable by reacting the triethylamine salt of α-aminophenylacetic acid with 2,3-dihydro-oxazolo-[4,5c]-pyridin-2-one) in 500 ml. of chloroform and the mixture is stirred overnight at 20°. It is then evaporated and the residue is dissolved in benzene and evaporated again. This procedure is repeated 3 times in all and the crude acid chloride thus obtained is used for the following reaction.

21.6 g. of APA and 70 ml. of triethylamine in 200 ml. of methylene chloride are stirred for 1 hour at 20°. The acid chloride, dissolved in 70 ml. of methylene chloride, is added dropwise, while stirring and cooling, to this solution and the mixture is stirred for a further hour at 20°. It is extracted repeatedly with water and the combined aqueous extracts are washed with ether and are adjusted to pH 2 with hydrochloric acid while stirring. The DL-α-(4-hydroxy-3-pyridyl-3-ureido)-benzylpenicillin which has precipitated is dried at 20°.

b. To obtain the potassium salt, the penicillin obtained in accordance with a) is dissolved at 0° in the calculated quantity of 0.5 N aqueous potassium hydroxide solution, the mixture is filtered and the filtrate is concentrated to dryness at 20°–30°.

EXAMPLE 7

25 ml. of thionyl chloride are added dropwise with cooling to a solution of 28.7 g. of D-2-(4-hydroxy-3-pyridyl-3-ureido)-phenylacetic acid in 500 ml. of DMF. The mixture is stirred for 2 hours at 20° and is evaporated under reduced pressure. The crude acid chloride thus obtained is reacted with APA analogously to Example 4, and D-α-(4-hydroxy-3-pyridyl-3-ureido)-benzylpenicillin is obtained.

EXAMPLE 8

1 ml. of ethyl chloroformate is added to 3.25 g. of the Na salt of DL-2-(4-hydroxy-3-pyridyl-3-ureido)-2-p-hydroxyphenylacetic acid in 50 ml. of dry acetone at −8° to −10°, and the mixture is stirred for one hour at −8° to −10°. The sodium chloride is then filtered off and the filtrate is added to a stirred solution of 2.54 g. of the K salt of APA in 30 ml. of water and 50 ml. of acetone. After stirring for one hour at 20°, the solvents are evaporated. The residue is taken up in 50 ml. of methanol. Undissolved matter is filtered off and the potassium salt of DL-α-(4-hydroxy-3-pyridyl-3-ureido)-p-hydroxybenzylpenicillin is precipitated from the filtrate by adding ether.

EXAMPLE 9

A suspension of 40.8 g. of DL-α-(4-hydroxy-3-pyridyl-3-ureido)-phenylacetic acid p-nitrophenyl ester (obtainable from the acid chloride and p-nitrophenol) in 300 ml. of chloroform is added dropwise, at 0°, to a solution of 29.8 g. of the triethylammonium salt of APA and 11.2 ml. of triethylamine in 450 ml. of chloroform and the mixture is then stirred for 2 hours at 20°. It is then evaporated at 30°, the residue is taken up in water/methyl isobutyl ketone, the pH is adjusted to 2.1 with sulfuric acid, the layers are separated and the aqueous layer is extracted again with methyl isobutyl ketone. The organic extracts are combined, washed with water and extracted repeatedly with sodium bicarbonate solution in such a way that the aqueous portion reaches a pH of 6.8–7.0. The phases are separated, the organic phase is extracted once more with water, and the combined aqueous phases are washed repeatedly with ether and evaporated at 20° to give the sodium salt of DL-α-(4-hydroxy-3-pyridyl-3-ureido)-benzylpenicillin.

EXAMPLE 10

A solution of 33 g. of 6-aminopenicillanic acid pivaloyloxymethyl ester, 20.6 g. of dicyclohexylcarbodiimide and 28.7 g. of α-(4-hydroxy-3-pyridyl-3-ureido)-phenylacetic acid in a mixture of 150 ml. of DMF and 150 ml. of dichloromethane is stirred for 2 hours at 20°. The dicyclohexylurea formed is filtered off and the filtrate is filtered through silica gel. Evaporation gives D-α-(4-hydroxy-3-pyridyl-3-ureido)-benzylpenicillin pivaloyloxymethyl ester.

EXAMPLE 11 a. 1 g. of D-α-(4-hydroxy-3-pyridyl-3-ureido)-benzylpenicillin trimethylsilyl ester (obtainable by reacting ampicillin successively with hexamethyldisilazane and with 2,3-dihydro-oxazolo-[4,5-c]pyridin-2-one) is shaken with 5 ml. of water for 30 minutes at 20° and the resulting D-α-(4-hydroxy-3-pyridyl-3-ureido)-benzylpenicillin is filtered off.

b. 5.86 g. of the triethylamine salt of D-α-(4-hydroxy-3-pyridyl-3-ureido)-benzylpenicillin are dissolved in 100 ml. of dichloromethane and 20 ml. of DMF; a solution of 1.51 g. of pivaloyloxymethyl chloride in 5 ml. of dichloromethane is added dropwise at 20°, while stirring, and the mixture is stirred for a further 2 hours at 20° and is washed with water. After drying and evaporation D-α-(4-hydroxy-3-pyridyl-3-ureido)-benzylpenicillin pivaloyloxymethyl ester is obtained, m.p. 161°–164°.

EXAMPLE 12

A suspension of 1 g. of D-α-(4-hydroxy-3-pyridyl-3-ureido)-benzylpenicillin benzyl ester (obtainable from ampicillin benzyl ester and 2,3-dihydro-oxazolo[4,5-c]pyridin-2-one), 0.2 g. of 10% palladium-on-charcoal and 100 ml. of methanol is shaken for 1 hour at 20° at atmospheric pressure, and the mixture is filtered and evaporated to give D-α-(4-hydroxy-3-pyridyl-3-ureido)-benzylpenicillin.

The following examples of pharmaceutical compositions containing compounds of Formula I are given by way of illustration:

Example A: Tablets

A mixture consisting of 2 kg. of D-α-(4-hydroxy-3-pyridyl-3-ureido)-benzylpenicillin, 5 kg. of lactose, 1.8 kg. of potato starch, 0.1 kg. of magnesium stearate and 0.1 kg. of talc is pressed into tablets in conventional manner, so as to form tablets each containing 200 mg. of active compound.

Example B: Dragees

Tablets are pressed analogously to Example A and are then coated in conventional manner with a coating consisting of sugar, potato starch, talc and tragacanth.

Example C: Capsules 5 kg. of D-α-(4-hydroxy-3-quinolyl-3-ureido)-benzylpenicillin are filled into hard gelatine capsules in conventional manner so as to form capsules each containing 500 mg. of the active compound.

Example D: Ampoules 500 g. of the sodium salt of D-α-(4-hydroxy-3-quinolyl-3-ureido)-benzylpenicillin is dissolved in 3 liters of twice-distilled water and the mixture is filtered under sterile conditions and then filled into ampoules. The solution in the ampoules is lyophilized and the ampoules are then closed under sterile conditions. Each ampoule contains 500 mg. of active compound.

Example E: Ampoules

Ampoules are prepared analogously to Example D, each ampoule containing 300 mg. of D-α-(4-hydroxy-3-quinolyl-3-ureido)-benzylpenicillin as the sodium salt and 100 mg. of cloxacillin as the sodium salt monohydrate.

Tablets, dragees, capsules and ampoules which contain one or more of the other compounds of Formula I, or their esters which can be readily hydrolyzed in vivo, or the physiologically acceptable salts of these compounds, can be made analogously.

The preceding examples can be repeated with similar success by substituting the generically or specifically described reactants and/or operating conditions of this invention for those used in the preceding examples.

From the foregoing description, one skilled in the art can easily acertain the essential characteristics of this invention, and without departing from the spirit and scope thereof, can make various changes and modifications of the invention to adapt it to various usages and conditions.

What is claimed is:

1. A penicillin of the formula

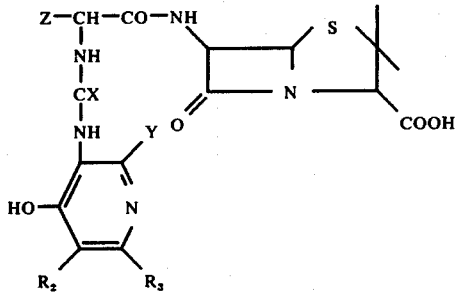

wherein X is O or S; Y is H or alkyl of 1–4 carbon atoms; Z is

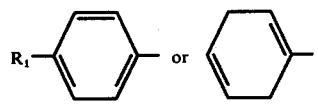

and $R_1$ is H or OH; and $R_2$ and $R_3$ each are H or collectively with the carbons to which they are attached form a first benzene or pyridine ring which is unsubstituted, which is substituted by up to two of alkyl, alkoxy of 1–4 carbon atoms, dialkylamino or halogen, wherein alkyl and alkoxy in each instance are of 1–4 carbon atoms, or which is fused at two adjacent carbons thereof directly to a second benzene or pyridine ring; or a conventional penicillin in vivo hydrolyzable and physiologically acceptable ester thereof; or physiologically acceptable salt of either.

2. A compound of claim 1, wherein X is O.
3. A compound of claim 1, wherein Z is phenyl.
4. A compound of claim 1, wherein Y is H.
5. A compound of claim 1, wherein $R_2$ and $R_3$ taken together with the carbons to which they are attached form a benzene or pyridine ring.
6. A compound of claim 1, wherein $R_2$ and $R_3$ each are H or together with the carbons to which they are attached form a benzene ring.
7. A compound of claim 1, wherein $R_2$ and $R_3$ together with the carbon atoms to which they are attached form a benzene or pyridine ring which is substituted at one carbon by methyl, methoxy, dimethylamino or chlorine and at a second carbon by methyl or chlorine or which is fused at two adjacent carbons thereof to form a pyridine ring.
8. A compound of claim 1, wherein X is O; Y is H; Z is phenyl or p-hydroxyphenyl; $R_2$ and $R_3$ each are H or together with the carbon atoms to which they are attached form a benzene or pyridine ring.
9. The compound of claim 8, wherein the benzene or pyridine ring is substituted by one of methyl, ethyl, methoxy, ethoxy, chlorine or bromine.
10. A compound of claim 1, wherein X is O; Y, $R_2$ and $R_3$ each are H and Z is phenyl or p-hydroxyphenyl.
11. A compound of claim 1, wherein X is O; Y is H; Z is phenyl or p-hydroxyphenyl and $R_2$ and $R_3$ together with the carbon atoms to which they are attached form a benzene ring.
12. A compound of claim 1, wherein X is O; Y is H; and $R_2$ and $R_3$ each are H or taken together with the carbon atoms to which they are attached form a benzene ring.
13. A compound of claim 1, wherein X is S; Y is H; and $R_2$ and $R_3$ each are H or taken together with the carbon atoms to which they are attached form a benzene ring.
14. A compound of claim 1, wherein the physiologically acceptable ester is an alkanoyloxymethyl of up to 6 carbon atoms in the alkanoyl.
15. D-α-(4-Hydroxy-3-pyridyl-3-ureido)-benzylpenicillin, a compound of claim 1.
16. D-α-(4-Hydroxy-3-quinolyl-3-ureido)-benzylpenicillin, a compound of claim 1.
17. D-α-(2-Methyl-4-hydroxy-3-quinolyl-3-ureido)-benzylpenicillin, a compound of claim 1.
18. D-α-(4-Hydroxy-6-methyl-3-quinolyl-3-ureido)-benzylpenicillin, a compound of claim 1.
19. D-α-(4-Hydroxy-6-chloro-3-quinolyl-3-ureido)-benzylpenicillin, a compound of claim 1.
20. D-α-(4-Hydroxy-6-bromo-3-quinolyl-3-ureido)-benzylpenicillin, a compound of claim 1.
21. D-α-(4-Hydroxy-6-dimethylamino-3-quinolyl-3-ureido)-benzylpenicillin, a compound of claim 1.
22. D-α-(4-Hydroxy-7-methyl-3-quinolyl-3-ureido)-benzylpenicillin, a compound of claim 1.
23. D-α-(4-Hydroxy-7-ethyl-3-quinolyl-3-ureido)-benzylpenicillin, a compound of claim 1,
24. D-α-(4-Hydroxy-7-methoxy-3-quinolyl-3-ureido)-benzylpenicillin, a compound of claim 1.
25. D-α-(4-Hydroxy-7-ethoxy-3-quinolyl-3-ureido)-benzylpenicillin, a compound of claim 1.
26. D-α-(4-Hydroxy-7-chloro-3-quinolyl-3-ureido)-benzylpenicillin, a compound of claim 1.

27. D-α-(4-Hydroxy-8-chloro-3-quinolyl-3-ureido)-benzylpenicillin, a compound of claim 1.
28. D-α-(4-Hydroxy-6,7-dimethyl-3-quinolyl-3-ureido)-benzylpenicillin, a compound of claim 1.
29. D-α-(4-Hydroxy-6,7-dichloro-3-quinolyl-3-ureido)-benzylpenicillin, a compound of claim 1.
30. D-α-(4-Hydroxy-6-methyl-7-chloro-3-quinolyl-3-ureido)-benzylpenicillin, a compound of claim 1.
31. D-α-[4-Hydroxy-3-(1,5-naphthyridyl)-3-ureido]-benzylpenicillin, a compound of claim 1.
32. D-α-[4-Hydroxy-3-(1,6-naphthyridyl)-3-ureido]-benzylpenicillin, a compound of claim 1.
33. D-α[4-Hydroxy-3(1,7-naphthyridyl)-3-ureido]-benzylpenicillin, a compound of claim 1.
34. D-α-[4-Hydroxy-3-(1,8-naphthyridyl)-3-ureido]-benzylpenicillin, a compound of claim 1.
35. D-α-[4-Hydroxy-3-(1,10-phenanthrolyl)-3-ureido]-benzylpenicillin, a compound of claim 1.
36. D-α-(4-Hydroxy-3-pyridyl-3-ureido)-benzylpenicillin pivaloyloxymethyl ester, a compound of claim 1.
37. D-α-(4-Hydroxy-3-quinolyl-3-ureido)-benzylpenicillin pivaloyloxymethyl ester, a compound of claim 1.
38. D-α-(2-Methyl-4-hydroxy-3-quinolyl-3-ureido)-benzylpenicillin pivaloyloxymethyl ester, a compound of claim 1.
39. D-α(4-Hydroxy-6-methyl-3-quinolyl-3-ureido)-benzylpenicillin pivaloyloxymethyl ester, a compound of claim 1.
40. D-α-(4-Hydroxy-6-chloro-3-quinolyl-3-ureido)-benzylpenicillin pivaloyloxymethyl ester, a compound of claim 1.
41. D-α-(4-Hydroxy-6-bromo-3-quinolyl-3-ureido)-benzylpenicillin pivaloyloxymethyl ester, a compound of claim 1.
42. D-α-(4-Hydroxy-6-dimethylamino-3-quinolyl-3-ureido)-benzylpenicillin pivaloyloxymethyl ester, a compound of claim 1.
43. D-α-(4-Hydroxy-7-methyl-3-quinolyl-3-ureido)-benzylpenicillin pivaloyloxymethyl ester, a compound of claim 1.
44. D-α-(4-Hydroxy-7ethyl-3-quinolyl-3-ureido)-benzylpenicillin pivaloyloxymethyl ester, a compound of claim 1.
45. D-α-(4-Hydroxy-7-methoxy-3-quinolyl-3-ureido)-benzylpenicillin pivaloyloxymethyl ester, a compound of claim 1.
46. D-α-(4-Hydroxy-7-ethoxy-3-quinolyl-3-ureido)-benzylpenicillin pivaloyloxymethyl ester, a compound of claim 1.
47. D-α-(4-Hydroxy-7-chloro-3-quinolyl-3-ureido)-benzylpenicillin pivaloyloxymethyl ester, a compound of claim 1.
48. D-α-(4-Hydroxy-8-chloro-3-quinolyl-3-ureido)-benzylpenicillin pivaloyloxymethyl ester, a compound of claim 1.
49. D-α-(4-Hydroxy-6,7-dimethyl-3-quinolyl-3-ureido)-benzylpenicillin pivaloyloxymethyl ester, a compound of claim 1.
50. D-α-(4-Hydroxy-6,7-dichloro-3-quinolyl-3-ureido)-benzylpenicillin pivaloyloxymethyl ester, a compound of claim 1.
51. D-α-(4-Hydroxy-6-methyl-7-chloro-3-quinolyl-3-ureido)-benzylpenicillin pivaloyloxymethyl ester, a compound of claim 1.
52. D-α-[4-Hydroxy-3-(1,5-naphthyridyl)-3-ureido]-benzylpenicillin pivaloyloxymethyl ester, a compound of claim 1.
53. D-α-[4-Hydroxy-3-(1,6-naphthyridyl)-3-ureido]-benzylpenicillin pivaloyloxymethyl ester, a compound of claim 1.
54. D-α-[4-Hydroxy-3-(1,7-naphthyridyl)-3-ureido]-benzylpenicillin pivaloyloxymethyl ester, a compound of claim 1.
55. D-α-[4-Hydroxy-3-(1,8-naphthyridyl)-3-ureido]-benzylpenicillin pivaloyloxymethyl ester, a compound of claim 1.
56. D-α-[4-Hydroxy-3-(1,10-phenanthrolyl)-3-ureido]- benzylpenicillin pivaloyloxymethyl ester, a compound of claim 1.
57. D-α-(4-Hydroxy-3-pyridyl-3-ureido)-p-hydroxy-benzylpenicillin, a compound of claim 1.
58. D-α-(4-Hydroxy-3-quinolyl-3-ureido)-p-hydroxy-benzylpenicillin, a compound of claim 1.
59. D-α-(2-Methyl-4-hydroxy-3-quinolyl-3-ureido)-p-hydroxybenzylpenicillin, a compound of claim 1.
60. D-α-(4-Hydroxy-6-methyl-3-quinolyl-3-ureido)-p-hydroxybenzylpenicillin, a compound of claim 1.
61. D-α-(4-Hydroxy-6-chloro-3-quinolyl-3-ureido)-p-hydroxybenzylpenicillin, a compound of claim 1.
62. D-α-(4-Hydroxy-6-bromo-3-quinolyl-3-ureido)-p-hydroxybenzylpenicillin, a compound of claim 1.
63. D-α-(4-Hydroxy-6-dimethylamino-3-quinolyl-3-ureido)-p-hydroxybenzylpenicillin, a compound of claim 1.
64. D-α-(4-Hydroxy-7-methyl-3-quinolyl-3-ureido)-p-hydroxybenzylpenicillin, a compound of claim 1.
65. D-α-(4-Hydroxy-7-ethyl-3-quinolyl-3-ureido)-p-hydroxybenzylpenicillin, a compound of claim 1.
66. D-α-(4-Hydroxy-7-methoxy-3-quinolyl-3-ureido)-p-hydroxybenzylpenicillin, a compound of claim 1.
67. D-α-(4-Hydroxy-7-ethoxy-3-quinolyl-3-ureido)-p-hydroxybenzylpenicillin, a compound of claim 1.
68. D-α-(4-Hydroxy-7-chloro-3-quinolyl-3-ureido)-p-hydroxybenzylpenicillin, a compound of claim 1.
69. D-α-(4-Hydroxy-8-chloro-3-quinolyl-3-ureido)-p-hydroxybenzylpenicillin, a compound of claim 1.
70. D-α-(4-Hydroxy-6,7-dimethyl-3-quinolyl-3-ureido)-p-hydroxybenzylpenicillin, a compound of claim 1.
71. D-α-(4-Hydroxy-6,7-dichloro-3-quinolyl-3-ureido)-p-hydroxybenzylpenicillin, a compound of claim 1.
72. D-α-(4-Hydroxy-6-methyl-7-chloro-3-quinolyl-3-ureido)-p-hydroxybenzylpenicillin, a compound of claim 1.
73. D-α-[4-Hydroxy-3-(1,5-naphthyridyl)-3-ureido]-p-hydroxybenzylpenicillin, a compound of claim 1.
74. D-α-[4-Hydroxy-3-(1,6-naphthyridyl)-3-ureido]-p-hydroxybenzylpenicillin, a compound of claim 1.
75. D-α-[4-Hydroxy-3-(1,7-naphthyridyl)-3-ureido]-p-hydroxybenzylpenicillin, a compound of claim 1.
76. D-α-[4-Hydroxy-3-(1,8-naphthyridyl)-3-ureido]-p-hydroxybenzylpenicillin, a compound of claim 1.
77. D-α-[4-Hydroxy-3-(1,10-phenanthrolyl)-3-ureido]-p-hydroxybenzylpenicillin, a compound of claim 1.
78. D-α-(4-Hydroxy-3-pyridyl-3-ureido) -1,4-cyclohexadienylmethylpenicillin, a compound of claim 1.
79. D-α-(4-Hydroxy-3-quinolyl-3-ureido)-1,4-cyclohexadienylmethylpenicillin, a compound of claim 1.

80. D-α-(2-Methyl-4-hydroxy-3-quinolyl-3-ureido)-1,4-cyclohexadienylmethylpenicillin, a compound of claim 1.

81. D-α-(4-Hydroxy-6-methyl-3-quinolyl-3-ureido)-1,4-cyclohexadienylmethylpenicillin, a compound of claim 1.

82. D-α-(4-Hydroxy-6-chloro-3-quinolyl-3-ureido)-1,4-cyclohexadienylmethylpenicillin, a compound of claim 1.

83. D-α-(4-Hydroxy-6-dimethylamino-3-quinolyl-3-ureido)-1,4-cyclohexadienylmethylpenicillin, a compound of claim 1.

84. D-α-(4-Hydroxy-7-ethyl-3-quinolyl-3-ureido)-1,4-cyclohexadienylmethylpenicillin, a compound of claim 1.

85. D-α-(4-Hydroxy-7-ethoxy-3-quinolyl-3-ureido)-1,4-cyclohexadienylmethylpenicillin, a compound of claim 1.

86. D-α-(4-Hydroxy-6,7-dimethyl-3-quinolyl-3-ureido)-1,4-cyclohexadienylmethylpenicillin, a compound of claim 1.

87. D-α-(4-Hydroxy-6,7-dichloro-3-quinolyl-3-ureido)-1,4-cyclohexadienylmethylpenicillin, a compound of claim 1.

88. D-α-(4-Hydroxy-6-methyl-7-chloro-3-quinolyl-3-ureido)-1,4-cyclohexadienylmethylpenicillin, a compound of claim 1.

89. D-α-[4-Hydroxy-(1,7-naphthyridyl)-3-ureido]-1,4-cyclohexadienylmethylpenicillin, a compound of claim 1.

90. D-α-[4-Hydroxy-(1,10phenanthrolyl)-3-quinolyl-3-ureido]-1,4-cyclohexadienylmethylpenicillin, a compound of claim 1.

91. D-α(4-Hydroxy-3-pyridyl-4-thioureido)-benzylpenicillin, a compound of claim 1.

92. D-α-(4-Hydroxy-3-quinolyl-4-thioureido)-benzylpenicillin, a compound of claim 1.

93. D-α-(4-Hydroxy-3-pyridyl-4-thioureido)-benzylpenicillin pivaloyloxymethyl ester, a compound of claim 1.

94. D-α-(4-Hydroxy-3-quinolyl-4-thioureido)-benzylpenicillin pivaloyloxymethyl ester, a compound of claim 1.

95. D-α-(4-Hydroxy-3-pyridyl-4-thioureido)-p-hydroxybenzylpenicillin, a compound of claim 1.

96. D-α-(4-Hydroxy-3-quinolyl-4-thioureido)-p-hydroxybenzylpenicillin, a compound of claim 1.

97. D-α-(4-Hydroxy-3-pyridyl-4-thioureido)-1.4-cyclohexadienylmethylpenicillin, a compound of claim 1.

98. D-α-(4-Hydroxy-3-quinolyl-4-thioureido)-1,4-cyclohexadienylmethylpenicillin, a compound of claim 1.

99. An antibacterial pharmaceutical composition comprising, in unit dosage form, an antibacterially effective amount per unit dosage of a compound of claim 1, in admixture with a pharmaceutically acceptable carrier.

100. A method of treating bacterial infections which comprises administering to the affected patient an antibacterially effective amount of a compound of claim 1.

* * * * *